United States Patent [19]

Morrison et al.

[11] Patent Number: 5,763,742
[45] Date of Patent: Jun. 9, 1998

[54] DETERMINATE, DELAYED-RIPENING CHERRY TOMATO PLANTS

[75] Inventors: Robert Morrison, Pleasanton; Allan Nash, Walnut Creek, both of Calif.

[73] Assignee: DNA Plant Technology Corporation, Oakland, Calif.

[21] Appl. No.: 544,574

[22] Filed: Oct. 18, 1995

[51] Int. Cl.$^6$ ............................ A01H 5/00; A01H 5/10; A01H 1/04
[52] U.S. Cl. ........................ 800/200; 800/205; 800/250; 800/255; 800/DIG. 44; 47/58; 47/DIG. 1
[58] Field of Search ........................... 800/200, 250, 800/DIG. 44, 205, 255; 47/58, DIG. 1

[56] References Cited

U.S. PATENT DOCUMENTS 4,843,186  6/1989  Nahum .................................. 800/1

OTHER PUBLICATIONS

McGlasson et al. Yield and evaluation of F1 tomato hybrids incorporating the non–ripening nor gene. Aust. J. Exp. Agric. Anim. Husb. 23:106–112, 1983.
Publication of Stokes "Growers Guide". P. 51 1991.
Stevens, M. Allen, (1986) "Inheritance of Tomato Fruit Quality Components", *Plant Breeding Reviews*, 4:273–311.
Tigchelaar, Edward C., (1986) "Tomato Breeding", *Breeding Vegetable Crops*, Ed. Mark J. Bassett, AVI Publishing Co., Inc, Westport, Connecticut, Chapter 4.
Publication of Zeraim Company, Israel, re Fresh Market Hybrid Tomatoes, 9 pages.
Publication of Siegers Seed Co., Zeeland, Michigan, re tomato seed, 2 pages.
Baggett, J.R. and Kean, D., "'Gold Nugget' Tomato," *HortScience* 20(5):957–958 (1985).
Publication of Tomato Growers Supply Company, Fort Myers, Florida, re available tomato seed and books on tomatoes, 5 pages.
Publication of Rogers NK Seed Company, Boise, Idaho, re varieties of tomatoes, 4 pages.
Kemble, J.M. and Gardner, R.G., "Inheritance of Shortened Fruit Maturation in the Cherry Tomato Cornell 871213–1 and Its Relation to Fruit Size and Other Components of Earliness," *J. Amer. Soc. Hort. Sci.* 117(4):646–650 (1992).
Mutschler, M.A. and Guttieri, M., "The Effects of the alc Mutant on Tomato Ripening," *Tomato Biotechnology*, 289–297 (1987).
Publication of Zeraim Gedera Company, Gedera, Israel, "Vetgetable and Field–Crop Varieties," 3 pages.

*Primary Examiner*—David T. Fox
*Assistant Examiner*—Melissa L. Kimball
*Attorney, Agent, or Firm*—Townsend and Townsend and Crew LLP

[57] ABSTRACT

The present invention provides determinate, delayed-ripening cherry tomato plants. The plants are hybrids, such as line 94478 (ATCC Accession No. 97315), derived from the determinate, non-ripening parental line 91047-15 (ATCC Accession No. 97316).

12 Claims, No Drawings

DETERMINATE, DELAYED-RIPENING CHERRY TOMATO PLANTS

FIELD OF THE INVENTION

The present invention relates generally to the breeding and development of tomato plants. More specifically, the invention relates to new hybrid cherry tomato plants having both a determinate habit and delayed-ripening fruit.

BACKGROUND OF THE INVENTION

Tomato plants having a determinate growth habit are particularly desired by growers because the plants are shorter and have an earlier, concentrated flowering. This growth habit is generally recognized as being conferred by the presence of the sp allele (Tigchelaar, Tomato Breeding In: M. J. Bassett, ed. *Breeding Vegetable Crops* AVI, Westport, Conn., 1986). The determinate trait is important from an economic standpoint since concentrated flowering results in concentrated fruit set which translates to reduced harvest costs because more fruit are picked per harvest. In extreme northern and southern latitudes, full yield potential is not realized from indeterminate varieties due to the occurrence of frost. In tropical and sub-tropical areas, full yield potential is not fully realized from indeterminate varieties due to the onset of disease. In each of these situations, the use of determinate varieties increases the probability of realizing full yield potential.

Most commercial cherry tomato varieties are indeterminate (e.g., Red Cherry, Large, Cherry Sweet, Sweet 100, and Sweet Chelsea). Several determinate commercial cherry tomato varieties have been developed (e.g., Baxter's Early Bush, Cherry Grande, and Mountain Bell which are available from e.g., Tomato Growers Supply Co., Fort Meyers, Fla. and Rogers NK Seed Co., Boise, Idaho). More recently new determinate cherry tomato varieties have been developed (e.g., EY 12, EY 14, EY 15, Zeraim Gedera, Gedera, Israel) but their status as commercial or garden varieties has not been established.

Another desirable trait in tomato cultivars is delayed-ripening fruit. BR 124, BR 140 (available from Hazera Seed Co., Rehovot, Israel) and FA 138 (available from Zeraim Gedera, Gedera, Israel) are known ripening-delayed cherry tomato varieties. All of these varieties are indeterminate.

In tomato, the main value of non-ripening or ripening-delayed fruit relates to fruit quality (flavor, shelf life) and durability. Since vine-ripened fruit of normal tomato varieties often cannot survive the rigors of harvesting, packing, and shipping (due to loss of firmness), the main tomatoes available in the market place are picked at the green stage when they are most firm, but have not yet reached peak flavor. Ripening-delay allows the tomato to reach the peak in flavor yet still retain sufficient firmness to survive harvest, packing, and shipping.

In tomato, several mutations have been reported to slow or inhibit ripening. These include dg, Nr, nor, and rin (Tigchelaar and Stevens, *Plant Breeding Reviews* 4:273–311 (1986)). These mutations are believed to interrupt the normal climacteric ripening pattern of tomato fruit. The best characterized of these mutations are nor and rin. In terms of inheritance and phenotype, both mutations are similar. In the homozygous state, nor and rin fruit do not fully ripen and are hence referred to as non-ripening plants. In the heterozygous state these mutations result in delayed-ripening (compared to normal ripening of wild type fruit). This intermediate phenotype means that the mutations are semi-dominant (Kopeliovitch et al., *J. Amer. Soc. Hort. Sci.* 107(3):361–364 (1982)). The ripening inhibition reported in the tomato line Alcobaca has been shown to be caused by a mutation that is an allele of nor (Lobo et al. *J. Amer. Soc. Hort. Sci.* 109:741–745 (1984)). The mutation Nr results in fruit that do not ripen fully (only to a pale orange) and may be the basis for the long shelf life of the variety Longkeeper. The mutation dg has not been as well characterized as the other mutations. The mutation appears to delay fruit softening (Tong et al., *J. Amer. Soc. Hort. Sci.* 114:635–638 (1989)).

Several determinate, ripening-delayed large-fruited tomato varieties are known (e.g., BR 84 (Hazera Seed Co.), Pik Ripe based on rin (Peto Seed Co., Saticoy, Calif.) and Lenor and Elenor based on nor (Pioneer Seed Co., Woodland, Calif.)). The prior art, however, lacks determinate, ripening-delayed cherry tomato varieties. The present invention addresses these and other needs.

Definitions

As used herein the term "cherry tomato" is used to refer to tomato varieties which have ripe fruit weight in the range of about 10 to about 30 grams, typically between about 15 and about 25 grams. The ripe fruit have a diameter between about 1.9 to about 3.8 cm, typically between about 2.5 and 3.0 cm. The shape of cherry tomato fruit are usually globe to slightly elliptical (i.e., fruit width and fruit length are about equivalent). Cherry tomato fruit differ from small-fruited pear-type varieties in that pear fruit are fully elliptical (i.e., fruit length is greater than fruit width) and from other varieties by virtue of lower fruit weight and fruit diameter.

Cherry tomatoes are sometimes designated as *Lycopersicon esculentum* var. *cerasiforme*. It is generally accepted that cultivated tomato lines were derived from var. *cerasiforme* via domestication (Jenkins, *Econ. Bot.* 2:379–392 (1948)). The main differences between the *cerasiforme* type and standard tomato cultivars is that the fruit of the *cerasiforme* types are less than half the size of the cultivated forms (see, Rick *Econ. Bot.* 12:346–367 (1958)). The *cerasiforme* types can also be distinguished from the cultivated types by the presence of a slightly exserted stigma in the flowers (Taylor, *Biosystematics of The Tomato*. In: Atherton and Rudich, eds. *The Tomato Crop*. Chapman and Hall, N. Y., N.Y., 1986). Smaller fruit size is probably the main reason that some cherry tomato varieties are designated as *cerasiforme* types.

The term "determinate habit" is used herein to refer to growth of tomato varieties which have two or fewer nodes between inflorescences. Plants having a determinate habit can be distinguished from indeterminate types, which have three or more nodes between each inflorescence (see, Tigchelaar, supra).

As used herein, the terms "delayed-ripening" or "ripening-delayed" are used to refer to tomato plants which are heterozygous for an allele which inhibits the maturation of fruit of the plant. Fruit of plants that are homozygous for the allele do not ripen and are referred to as non-ripening. As discussed above, such alleles include dg, Nr, nor, and rin. Generally, ripening-delayed tomatoes of the invention are distinguished from normal-ripening plants in that at least 50% more marketable fruit remain after 15 days of storage at 20° C. in ripening-delayed plants. The precise phenotype of a plant having the ripening-delayed trait will depend upon the particular gene. A summary of phenotypes of plants having various alleles is summarized in Table 1.

TABLE 1

Tomato ripening-mutants

| Name | Chromosome | Phenotype of fruit homozygous for the mutation |
| --- | --- | --- |
| Ripening inhibitor (rin) | 5 | Fruit do not fully ripen fully and soften very slowly. Final fruit color is yellow Fruit lack normal tomato flavor and store for a very long time. |
| Non-ripening (nor) | 10 | Similar to rin but final fruit color is pale orange. |
| Never-ripe (Nr) | 9 | Final fruit color is orange and soften slowly. |
| Greenflesh (gf) | 8 | Ripe fruit appear red-brown in color. Chlorophyll loss is incomplete. |
| Yellowflesh (r) | 3 | Ripe fruit are yellow. Lycopene is not synthesized. Fruit are otherwise normal. |
| Alcobaca (alc) | 10 | Fruit ripened attached to the vine are pale red. The flavor is almost normal but storability is increased due to a slow softening rate. Fruit picked mature green show reduced ethylene production and respiration. Ripen to a yellow color. |
| Longkeeper | 10 | Fruit ripen to a golden-orange-red color. Polygalacturonase activity, softening and carotenoid synthesis are much reduced. Fruit store for a long time. |
| Tangerine (t) | 10 | Fruit are a rich tangerine color owing to the replacement of lycopene by prolycopene. The fruit are otherwise normal. |
| Uniform ripening (u) | 10 | Immature fruit lack dark-green shoulder. |

(From Grierson and Kader Fruit Ripening and Quality In: Atherton and Rudich, eds. The Tomato Crop. Chapman and Hail, NY, NY, 1986).

As used herein a plant, seed, or fruit is "derived from" a second plant if it is arises directly or indirectly from the second plant. Thus, a derived plant may be an $F_1$, or more removed generation produced by standard breeding techniques using the second plant as parent. Alternatively, the derived plant may result from in vitro culture of tissue from the second plant using standard tissue culture and plant regeneration techniques.

SUMMARY OF THE INVENTION

The present invention provides hybrid cherry tomato plants having a determinate growth habit and delayed-ripening fruit. Usually, the plants of the invention result from crossing a first inbred cherry tomato plant having a determinate growth habit with a second cherry tomato plant from an inbred line having a determinate growth habit and non-ripening fruit. A preferred line for this purpose is 91047-15 (ATCC Accession No.97316). As used herein a line is considered to be inbred even if it is an "open pollinated" line as a result of open field seed production.

The first parental line can be any commercially available or proprietary cherry tomato that has a determinate growth habit. An exemplary line is NC 2C.

An exemplary hybrid produced from such lines is 94478 (ATCC Accession No.97315). The invention also provides cherry tomato fruit and seed produced by such hybrids or the parental non-ripening lines. In addition, the invention provides cherry tomato seed which can be grown to yield a hybrid plant of the invention.

The invention further provides methods of making a hybrid cherry tomato having a determinate growth habit and delayed-ripening fruit. The methods comprise crossing a first cherry tomato plant having a determinate growth habit with a second cherry tomato plant from an inbred line having a determinate growth habit and non-ripening fruit. $F_1$ plants which have a determinate growth habit and delayed-ripening fruit are then selected.

DESCRIPTION OF THE PREFERRED EMBODIMENTS

The hybrids of the invention are produced from crossing a first determinate parental line with a second determinate, non-ripening parental line. A suitable second parental line is produced by crossing and pedigree selection to identify progeny having the desired traits. In particular, a second parent line used to make hybrids of the invention should be homozygous for a mutation conferring a non-ripening trait (e.g., rin or nor). A preferred line for this purpose is inbred line 91047-15 (seed from this line have been deposited with the American Type Culture Collection, Rockville Md.) on Oct. 13, 1995. This line was identified in the $F_3$ generation of a BR 124 segregating population when test-cross hybrids between randomly selected $F_3$ plants were crossed with Baxter's Early Bush. BR 124 is an indeterminate hybrid between a non-ripening line and a normal ripening line. It is heterozygous for the sp allele which confers determinate growth habit.

The 91047-15 or other (second) parental line can be used to produce hybrid cherry tomato plants having a determinate growth habit and delayed-ripening fruit. The methods of the invention can be used to produce cherry tomato hybrid plants with any other desired characteristics, such as disease resistance, improved tomato flavor, and the like. Typically, the methods involve crossing a suitable first parental cherry tomato line, having a determinate habit conferred by the presence of the sp allele, with a second determinate, non-ripening parental line. Suitable lines for the first parental line include, but are not limited to, NC 1C and NC 2C (available from North Carolina State University), Baxter's Early Bush, Cherry Grande, and Mountain Bell (available from e.g., Tomato Growers Supply Co., Fort Meyers, Fla. and Rogers NK Seed Co., Boise, Idaho). In some embodiments, the second parental line can be the male parent as described for instance in U.S. Pat. No. 4,843,186.

The $F_1$ generation is then examined for the presence of determinate habit and delayed fruit ripening in a single plant. The determinate trait is identified by determining the number of nodes between each inflorescence. Determinate plants will have two or fewer nodes, indeterminate plants will have three or more nodes. The delayed-ripening trait will be identified by slower ripening as compared to wild-type plants.

As noted above, the second parental line is homozygous for an allele conferring the non-ripening trait. Thus, hybrids made with plants lacking this trait have a delayed-ripening phenotype. The terms used herein to describe ripeness of tomato fruit are according to standard ripeness classes as described, for instance, in The Tomato Crop Atherton and Rudich eds. (Chapman Hall, 1986). The ripeness classes for a given fruit are set forth in Table 2.

TABLE 2

| Score | Class | Description |
| --- | --- | --- |
| 1 | Green | Entirely light to dark-green, but mature. |
| 2 | Breaker | First appearance of external pink, red or tannish-yellow color, not more than 10%. |
| 3 | Turning | Over 10%, but not more than 30% red, pink or tannish-yellow. |

TABLE 2-continued

| Score | Class | Description |
|---|---|---|
| 4 | Pink | Over 30%, but not more than 60% pinkish or red. |
| 5 | Light red | Over 60%, but not more than 90% red. |
| 6 | Red | Over 90% red, desirable table ripeness. |

In the second parental line, the non-ripening trait is typically characterized by fruit which do not turn fully red in color. Usually, even when fully mature the fruit are only yellow to yellow-pink in color. The trait is expressed in all fruit and the fruit will not break down due to senescence at the rate of a wild-type line. In the hybrid, full red color is reached but this occurs at a slower pace than with wild-type lines.

Production of an exemplary hybrid, 94478, is described below. Seed from this hybrid have been deposited with the American Type Culture Collection, Rockville Md.). This hybrid has a normal form, with a medium canopy and a semi-erect habit. The stem has intermediate branching. The leaf margin is shallowly toothed or scalloped and shows slight marginal rolling at about mid-season. The surface of major leaflets is rugose with normal pubescence. The inflorescences are compound, with an average of about 8 flowers per inflorescence. The flowers have yellow corollas and the calyx is normal with awl-shaped lobes, which are approximately equal in length to the corolla. The fruit have two to three locules and are round in transverse section. The stem and blossom ends are both flat. The pistil scar is a dot.

EXAMPLES

I. Production of parental line 910475-15

As noted above, 91047-15 is a selection from BR 124 based on test-cross performance and horticultural type. It is a determinate, non-ripening cherry tomato line with prolific fruit production.

To obtain the line, the hybrid BR 124 was self-pollinated and the resulting $F_2$ plants were selfed to obtain the $F_3$ generation. The population in each generation comprised about 1000 plants. Randomly chosen $F_3$ plants were used in test-crosses with Baxter's Early Bush. In addition to using pollen from the $F_3$ plants for the test crosses, each randomly selected plant was self-pollinated. Upon evaluation of the test hybrids in the field several determinate test hybrids were identified. This finding indicated that the BR 124 hybrid is heterozygous at the sp locus. It also allowed identification of a determinate line at least 12 months earlier than would have been possible using a conventional inbreeding method. The seed derived from selfing the $F_3$ plants was planted and the 91047-15 inbred line was selected. When growing the $F_4$ 91047-15 plants, the fruit were observed to be non-ripening.

II. Production of determinate, delayed-ripening hybrids

A crossing block was set up in the greenhouse to make useful hybrids for evaluation. These hybrids were made with the $F_4$ seed of the non-ripening determinate lines crossed to publicly available inbred cherry tomato lines. The subsequent hybrids were evaluated in the field.

A number of cherry tomato hybrids were produced using various determinate lines and the 91047-15 line as parents. A sensory panel concluded that 2 of these hybrids outperformed BR 124 in sensory evaluations. One such hybrid, 94478, is a cross of NC 2C and 91047-15. A second hybrid, 94475, is a cross between 91150 and 91047-15 (91150 is a selection from P860279-2 obtained from Jay Scott at the University of Florida).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A hybrid cherry tomato plant having a determinate growth habit and delayed-ripening fruit, the plant resulting from crossing a first cherry tomato plant having a determinate growth habit with a second cherry tomato plant having a determinate growth habit and non-ripening fruit, wherein said second cherry tomato plant is from line 91047-15 (ATCC Accession No. 97316).

2. The hybrid plant of claim 1, wherein the first cherry tomato plant is NC 2C.

3. The hybrid plant of claim 1, which is 94478 (ATCC Accession No. 97315).

4. Cherry tomato seed which can be grown to yield a hybrid plant of claim 1.

5. Inbred cherry tomato line 91047-15 (ATCC Accession No. 97316).

6. Cherry tomato seed from a plant of the cherry tomato line of claim 5.

7. A cherry tomato plant derived from the cherry tomato line of claim 5.

8. Hybrid cherry tomato plant 94478 (ATCC Accession No. 97315).

9. Cherry tomato seed from the plant of claim 8.

10. A method of making a hybrid cherry tomato having a determinate growth habit and delayed-ripening fruit, the method comprising crossing a first cherry tomato plant having a determinate growth habit and a second cherry tomato plant from line 91047-15 (ATCC Accession No. 97316); and selecting $F_1$ plants which have a determinate growth habit and delayed-ripening fruit.

11. The method of claim 10, wherein the first cherry tomato plant is NC 2C.

12. A cherry tomato plant obtained by the method of claim 10.

* * * * *